United States Patent
Nakano et al.

[11] Patent Number: 6,037,507
[45] Date of Patent: Mar. 14, 2000

[54] OXIDATION PROCESS OF BRANCHED ALIPHATIC HYDROCARBONS AND PROCESS FOR PRODUCING THE OXIDE

[75] Inventors: Tatsuya Nakano, Himeji; Yasutaka Ishii, Takatsuki, both of Japan

[73] Assignees: Daicel Chemical Industries, Ltd.; Yasutaka Ishii, both of Osaka, Japan

[21] Appl. No.: 09/037,703

[22] Filed: Mar. 10, 1998

[30] Foreign Application Priority Data

Mar. 11, 1997 [JP] Japan ..................................... 9-056517
Aug. 5, 1997 [JP] Japan ..................................... 9-210973

[51] Int. Cl.$^7$ ............................ C07C 29/50; C07C 31/04
[52] U.S. Cl. ....................... 568/910.5; 568/910; 568/399; 568/915; 502/161; 502/222
[58] Field of Search .................................... 568/571, 382, 568/383, 399, 398.8, 840, 909.8, 910, 910.5, 915; 502/161, 209, 219, 220, 221, 222, 223

[56] References Cited

U.S. PATENT DOCUMENTS 4,294,999  10/1981  Grane et al. ............................ 568/910

FOREIGN PATENT DOCUMENTS 838909A  2/1996  Japan .

OTHER PUBLICATIONS

"Lecture Draft II", The 67$^{th}$ Spring Annual Meeting (1994) of Chemical Society of Japan, p. 762.
Ishii et al., *J. Org. Chem.*, 61, pp. 4520–4526 (1996).

Primary Examiner—Gary Geist
Assistant Examiner—Sreeni Padmanabhan
Attorney, Agent, or Firm—Birch, Stewart, Kolasch & Birch, LLP

[57] ABSTRACT

A non-cyclic branched aliphatic hydrocarbon (e.g., isobutane) is oxidized with oxygen in the presence of an oxidation catalyst comprising an imide compound of the following formula (1) (e.g., N-hydroxyphthalimide) or an oxidation catalyst comprising the imide compound and a co-catalyst (e.g., a transition metal compound of selected from Group 3A, 4A, 5A, 6A, 7A, 8 and 1B elements of the Periodic Table of elements), for the formation of an oxide (e.g., t-butanol, acetone):

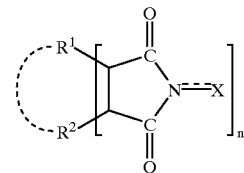

(1)

wherein $R^1$ and $R^2$ represent a substituent such as a hydrogen atom or a halogen atom, or $R^1$ and $R^2$ may together form a double bond or an aromatic or non-aromatic 5- to 12-membered ring, X is O or OH, and n is 1 to 3.

20 Claims, No Drawings

OXIDATION PROCESS OF BRANCHED ALIPHATIC HYDROCARBONS AND PROCESS FOR PRODUCING THE OXIDE

FIELD OF THE INVENTION

This invention relates to an oxidation process, which is useful for oxidation of a non-cyclic branched aliphatic hydrocarbon with oxygen to produce a corresponding alcohol or ketone, and to a process for producing the oxide.

BACKGROUND OF THE INVENTION

A tertiary alcohol such as t-butanol is characterized by high oxidation resistance and high reactivity of a hydroxyl group relative to a primary alcohol and a secondary alcohol. Therefore, the tertiary alcohol is broadly used as a petrol additive, a reaction reagent such as a tertiary butylation agent. The t-butanol is produced by acting a concentrated sulfuric acid on isobutene generated by cracking and so on, and hydrolyzing a generated sulfate with water. This process, however, requires treatment of sulfuric acid and reduces the reaction operability.

A preferred oxidation process from the viewpoints of resources and environment is a catalytic oxidation, which is conducted with direct use of molecular oxygen or air as an oxidizing agent. However, oxidation of a branched saturated hydrocarbon such as isobutane (e.g., $C_{4-6}$ fraction) with air provides a demethylated ketone and it is difficult to form a tertiary alcohol.

In page 762 of the "Lecture Draft II" (1994) of 67th Spring Annual Meeting of Chemical Society of Japan, it is reported that oxidation of an alcohol such as benzyl alcohol or benzhydrol with air using vanadomolybdophosphoriate and N-hydroxyphthalimide provides a ketone such as acetophenone or benzophenone in a high yield, and that oxidation of fluorene or adamantane with oxygen using N-hydroxyphthalimide gives a corresponding adamantanol or fluorenone.

SUMMARY OF THE INVENTION

It is, therefore, an object of the present invention to provide an oxidation reaction which insures efficient oxidation of a non-cyclic branched aliphatic hydrocarbon and provides a corresponding alcohol or ketone, and a process for producing an oxide.

It is another object of the invention to provide an oxidation reaction that inhibits deactivation of a catalyst, efficiently oxidizes a non-cyclic branched aliphatic hydrocarbon and provides a branched alcohol or ketone with high conversion and selectivity, and a process for producing such oxide.

A further object of the invention is to provide an oxidation reaction, which produces a tertiary alcohol by oxidation with oxygen, with high conversion and selectivity, and a process for producing the tertiary alcohol.

The present inventors did much investigation to accomplish the above objects, and as a result, found that oxidation of a non-cyclic aliphatic hydrocarbon (e.g., isobutane) with oxygen in the presence of an oxidation catalyst comprising an imide compound or an oxidation catalyst comprising the imide compound and a co-catalyst provides the corresponding branched alcohols (e.g., t-butanol) or ketones (e.g., acetone) efficiently. The present invention has been accomplished based on the above findings.

Thus, the oxidation process of the present invention comprises an oxidation of a substrate by contacting a non-cyclic branched aliphatic hydrocarbon (hereinafter may refer to as a substrate) with oxygen in the presence of an oxidation catalyst comprising an imide compound shown by the following formula (I),

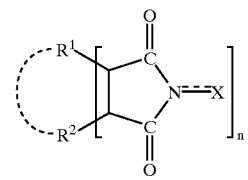

(1)

wherein $R^1$ and $R^2$ respectively represent a hydrogen atom, a halogen atom, an alkyl group, an aryl group, a cycloalkyl group, a hydroxyl group, an alkoxy group, a carboxyl group, an alkoxycarbonyl group, or an acyl group; or $R^1$ and $R^2$ may bond together to form a double bond, or an aromatic or non-aromatic ring; X represents an oxygen atom or a hydroxyl group; and n denotes an integer of 1 to 3, or an oxidation catalyst comprising the imide compound and a co-catalyst. In this process, the branched aliphatic hydrocarbon is preferably a saturated aliphatic hydrocarbon having a tertiary hydrogen atom. A ratio of the co-catalyst is, for instance, from not less than an effective amount to not more than 10 mole % relative to the imide compound. The co-catalyst comprises a compound containing an element selected from the group consisting of Group 2A elements of the Periodic Table of Elements, a transition metal and Group 3B elements of the Periodic Table of Elements.

A process for producing an oxide of the present invention (i.e., a process for producing an alcohol or a ketone) comprises contacting a non-cyclic branched aliphatic hydrocarbon with oxygen in the presence of the oxidation catalyst to provide a corresponding alcohol or ketone. This process may produce a corresponding alcohol to non-cyclic branched aliphatic hydrocarbon with high selectivity by contacting the branched aliphatic hydrocarbon with oxygen in the presence of a non-protic solvent.

Incidentally, the term "divalent transition metal compound" comprises a transition metal compound produced in a reaction system.

DETAILED DESCRIPTION OF THE INVENTION

[Imide compound]

In the compound shown by the formula (1), the halogen atom, as the substituents $R^1$ and $R^2$, includes iodine, bromine, chlorine and fluorine atoms. The alkyl group includes, for example, methyl, ethyl, propyl, isopropyl, butyl, isobutyl, sec-butyl, t-butyl, pentyl, hexyl, heptyl, octyl, decyl, or other straight chain or branched chain alkyl groups each having about 1 to 10 carbon atoms. An illustrative preferred alkyl group includes alkyl groups each having about 1 to 6 carbon atoms, in particular lower alkyl groups each having about 1 to 4 carbon atoms.

As the aryl group, there may be mentioned, for instance, a phenyl group and a naphthyl group. Examples of the cycloalkyl group include cyclopentyl, cyclohexyl, and cyclooctyl groups. The alkoxy group includes, for example, methoxy, ethoxy, propoxy, isopropoxy, butoxy, isobutoxy, t-butoxy, pentyloxy, hexyloxy, and other alkoxy groups each having about 1 to 10 carbon atoms. Among them, alkoxy groups each having about 1 to 6 carbon atoms, in particular lower alkoxy groups each having about 1 to 4 carbon atoms are desirable.

Examples of the alkoxycarbonyl group include methoxycarbonyl, ethoxycarbonyl, propoxycarbonyl, isopropoxycarbonyl, butoxycarbonyl, isobutoxycarbonyl, t-butoxycarbonyl, pentyloxycarbonyl, hexyloxycarbonyl, and other alkoxycarbonyl groups each having about 1 to 10 carbon atoms in the alkoxy moiety. A preferred alkoxycarbonyl group includes those each having about 1 to 6 carbon atoms in the alkoxy moiety, among which lower alkoxycarbonyl groups each having about 1 to 4 carbon atoms in the alkoxy moiety are typically desirable.

The acyl group includes, for instance, formyl, acetyl, propionyl, butyryl, isobutyryl, valeryl, iso-valeryl, pivaloyl, and other acyl groups each having about 1 to 6 carbon atoms.

The substituents $R^1$ and $R^2$ may be either the same or different from each other. In the formula (1), $R^1$ and $R^2$ may bond together to form a double bond, or an aromatic or non-aromatic ring. A preferred aromatic or non-aromatic ring may be a ring having about 5 to 12 members, in particular about 6 to 10 members. Such a ring may be a heterocyclic ring or a condensed heterocyclic ring, but it may practically be a hydrocarbon ring. As such a ring, there may be mentioned, for instance, non-aromatic alicyclic rings (e.g., cyclohexane ring and other cycloalkane rings which may have a substituent, cyclohexene ring and other optionally substituted cycloalkene rings), non-aromatic bridged (cross-linked) rings (e.g., 5-norbornene ring and other optionally substituted bridged hydrocarbon rings), benzene ring, naphthalene ring and other optionally substituted aromatic rings. The ring may practically comprise an aromatic ring.

A preferred imide compound includes compounds 5 shown by the following formula,

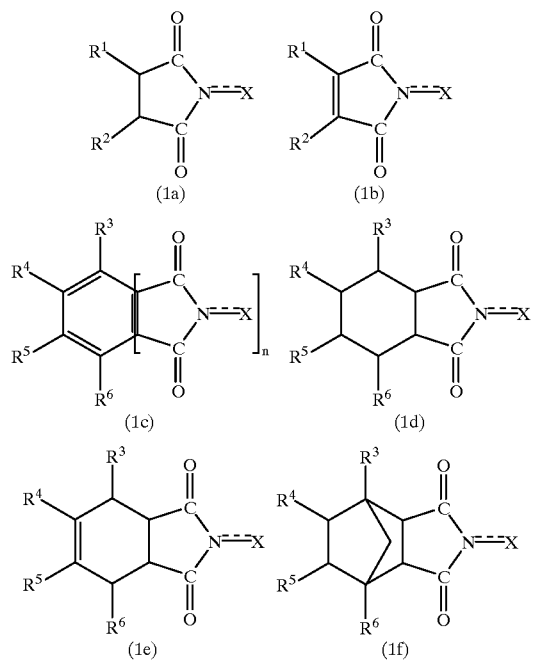

(1a) (1b) (1c) (1d) (1e) (1f)

wherein $R^3$ $R^4$, $R^5$ and $R^6$ independently represent a hydrogen atom, an alkyl group, a hydroxyl group, an alkoxy group, a carboxyl group, an alkoxycarbonyl group, an acyl group. a nitro group, a cyano group, an amino group or a halogen atom; the bond between the nitrogen atom "N" and "X" denotes a single bond or a double bond; and $R^1$, $R^2$, X and n have the same meanings as defined above.

In the substituents $R^3$, $R^4$, $R^5$ and $R^6$, the alkyl group includes alkyl groups similar to those exemplified above, in particular alkyl groups each having about 1 to 6 carbon atoms. The alkoxy group includes the same alkoxy groups as mentioned above, in particular lower alkoxy groups each having about 1 to 4 carbon atoms. Examples of the alkoxycarbonyl group include the same alkoxycarbonyl groups as exemplified above, in especial lower alkoxycarbonyl groups each having about 1 to 4 carbon atoms in the alkoxy moiety. As the acyl group, there may be mentioned the similar acyl groups to those mentioned above, in particular acyl groups each having about 1 to 6 carbon atoms. Examples of the halogen atom include fluorine, chlorine and bromine atoms. The substituents $R^3$, $R^4$, $R^5$ and $R^6$ may practically be hydrogen atoms, lower alkyl groups each having 1 to 4 carbon atoms, carboxyl groups, nitro groups or halogen atoms, respectively.

The symbol X in the formula (1) denotes an oxygen atom or a hydroxyl group. A bond between the nitrogen atom "N" and "X" is a single bond or a double bond. Further, n usually denotes about 1 to 3, preferably 1 or 2. The imide compound shown by the formula (1) can be used singly or in combination in the oxidation reaction.

As examples of the acid anhydride corresponding to the imide compound of the formula (1), there may be mentioned succinic anhydride, maleic anhydride, or other saturated or unsaturated aliphatic dicarboxylic acid anhydrides, tetrahydrophthalic anhydride, hexahydrophthalic anhydride (1,2-cyclohexanedicarboxylic anhydride), 1,2,3,4-cyclohexanetetracarboxylic acid 1,2-anhydride, and other saturated or unsaturated nonaromatic cyclic polycarboxylic acid anhydrides (alicyclic polycarboxylic anhydrides), hetic anhydride, himic anhydride, and other bridged cyclic polycarboxylic anhydrides (alicyclic polycarboxylic anhydrides), phthalic anhydride, tetrabromophthalic anhydride, tetrachlorophthalic anhydride, nitrophthalic anhydride, trimellitic anhydride, methylcyclohexenetricarboxylic anhydride, pyromellitic anhydride, mellitic anhydride, 1,8:4,5-naphthalenetetracarboxylic dianhydride, and other aromatic polycarboxylic anhydrides.

Examples of a preferred imide compound include N-hydroxysuccinimide, N-hydroxymaleimide, N-hydroxyhexahydrophthalimide, N,N'-dihydroxycyclohexanetetracarboximide, N-hydroxyphthalimide, N-hydroxytetrabromophthalimide, N-hydroxytetrachlorophthalimide, N-hydroxyhetimide, N-hydroxyhimimide (N-hydroxy-5-norbornen-2,3-dicarboximide), N-hydroxytrimellitimide, N,N'-dihydroxypyromellitimide, N,N'-dihydroxynaphthalenetetracarboximide and so forth. A typically preferable imide compound includes an N-hydroxyimide compound derived from an alicyclic polycarboxylic anhydride, in particular from an aromatic polycarboxylic anhydride, such as N-hydroxyphthalimide.

The imide compound may be prepared by a conventional imidation process (a process for the formation of an imide), such as a process that comprises the steps of allowing a corresponding acid anhydride to react with hydroxylamine $NH_2OH$ for ring-opening of an acid anhydride group, and closing the ring to form an imide.

These imide compounds have high oxidizing activities, and can efficiently oxidize a non-cyclic aliphatic hydrocarbon with air or with oxygen even in mild or moderate conditions. Particularly, when an oxidation catalyst comprises the amide compound and the co-catalyst in a combination, high activities are realized, the substrate can be oxidized efficiently even in mild or moderate conditions and a transformation rate or conversion and/or selectivity can be enhanced. Therefore, according to the present invention, the a substrate is efficiently oxidized in the presence of a catalyst comprising the imide compound or a catalytic system comprising the imide compound and the co-catalyst to give an alcohol and a ketone corresponding to the substrate with high selectivity.

[Co-catalyst]

A co-oxidizing agent as the co-catalyst includes or comprises metal compounds such as compound comprising or containing a Group 2A element of the Periodic Table of Elements (e.g., magnesium, calcium, strontium, barium), a transition metal compound, or compounds containing a Group 3B element (e.g., boron B, aluminium Al) of the Periodic Table of Elements. These co-catalysts may be employed independently or in combination.

As the elements of the transition metal, there may be mentioned, for instance, Group 3A elements of the Periodic Table of Elements (e.g., scandium Sc, yttrium Y, and lanthanum La, cerium Ce, samarium Sm and other lanthanoid elements, actinium Ac and other actinoid elements), Group 4A elements of the Periodic Table of Elements (e.g., titanium Ti, zirconium Zr, hafnium Hf), Group 5A elements (e.g., vanadium V, niobium Nb, tantalum Ta), Group 6A elements (e.g., chromium Cr, molybdenum Mo, tungsten W), Group 7A elements (e.g., manganese Mn, technetium Tc, rhenium Re), Group 8 elements (e.g., iron Fe, ruthenium Ru, osmium Os, cobalt Co, rhodium Rh, iridium Ir, nickel Ni, palladium Pd, platinum Pt), Group 1B elements (e.g., copper Cu, silver Ag, gold Au) and Group 2B elements of the Periodic Table of Elements (e.g., zinc Zn, cadmium Cd).

A preferred element of the co-catalyst includes elements of the transition metals (e.g., lanthanoid elements, actinoid elements and other Group 3A elements of the Periodic Table of Elements, Group 4A elements, Group 5A elements, Group 6A elements, Group 7A elements, Group 8 elements, Group 1B elements, and Group 2B elements of the Periodic Table of Elements) and Group 3B elements of the Periodic Table of Elements (e.g., boron compounds). In particular, high oxidizing activities are demonstrated when the imide compound of the formula (I) is used in combination with a compound containing Ti, Zr or other Group 4A elements, V or other Group 5A elements, Cr, Mo, W or other Group 6A elements, Mn, Tc, Re or other Group 7A elements, Fe, Ru, Co, Rh, Ni or other Group 8 elements, or Cu or other Group 1B elements.

The species of the co-catalyst is not particularly limited as far as it contains the element and has oxidizing property, and it may be a simple substance or hydroxide of a metal. The co-catalyst may practically be an oxide of a metal (a double oxide or an oxygen acid or a salt thereof), an organic acid salt, an inorganic acid salt, a halide, a coordinate compound (a complex) comprising the metal element, a polyacid (a heteropolyacid or an isopolyacid) or its salt.

As the boron compound, there may be mentioned, for example, a boron hydride (e.g., borane, diborane, tetraborane, pentaborane, decaborane), a boric acid (e.g., orthoboric acid, metaboric acid, tetraboric acid), a borate (e.g., a nickel borate, magnesium borate, manganese borate), $B_2O_3$, and other boron oxides, borazane, borazene, borazine, boron amide, boron imide, and other nitrogen-containing boron compounds, $BF_3$, $BCl_3$, tetrafluoroborate, and other halides, esters of boric acid (e.g., methyl borate, phenyl borate) and so on. A preferred boron compound includes boron hydrides, orthoboric acid, and other boric acids or salts thereof, among which a boric acid can preferably be employed. These co-catalysts may be employed singly or in combination.

The hydroxide includes $Mn(OH)_2$, $Mn(OH)$, $Fe(OH)_2$ and $Fe(OH)_3$, typically speaking. Examples of the metallic oxide include $Sm_2O_3$, $TiO_2$, $ZrO_2$, $V_2O_3$, $V_2O_5$, $CrO$, $Cr_2O_3$, $MoO_3$, $MnO$, $Mn_3O_4$, $Mn_2O_3$, $MnO_2$, $Mn_2O_7$, $FeO$, $Fe_2O_3$, $Fe_3O_4$, $RuO_2$, $RuO_4$, $CoO$, $CoO_2$, $Co_2O_3$, $RhO_2$, $Rh_2O_3$, $Cu_2O_3$, and so forth. As examples of the double oxide or oxygen acid salt, there may be mentioned $MnAl_2O_4$, $MnTiO_3$, $LaMnO_3$, $K_2Mn_2O_5$, $CaO.xMnO_2$ (=0.5, 1, 2, 3, 5), manganese salts [e.g., $Na_3MnO_4$, $Ba_3[MnO_4]_2$ and other manganates(V), $K_2MnO_4$, $Na_2MnO_4$, $BaMnO_4$, and other manganates(VI), $KMnO_4$, $NaMnO_4$, $LiMnO_4$, $NH_4MnO_4$, $CsMnO_4$, $AgMnO_4$, $Ca(MnO_4)_2$, $Zn(MnO_4)_2$, $Ba(MnO_4)_2$, $Mg(MnO_4)_2$, $Cd(MnO_4)_2$, and other permanganates].

As the organic acid salts, there may be exemplified as cobalt acetate, manganese acetate, cobalt propionate, manganese propionate, cobalt naphthenate, manganese naphthenate, cobalt stearate, manganese stearate, and other salts with a $C_{2-20}$ fatty acid, manganese thiocyanate, and corresponding salts of Ce, Ti, Zr, V, Cr, Mo, Fe, Ru, Ni, Pd, Cu and Zn. The inorganic acid salt includes, for instance, cobalt nitrate, iron nitrate, manganese nitrate, nickel nitrate, copper nitrate, and other nitrates, and sulfates, phosphates and carbonates each corresponding to these nitrates (e.g., cobalt sulfate, iron sulfate, manganese sulfate, cobalt phosphate, iron phosphate, manganese phosphate, an iron carbonate, a manganese carbonate, iron perchlorate). As the halides, there may be mentioned, for instance, $SmCl_3$, $SmI_2$, $TiCl_2$, $ZrCl_2$, $ZrOCl_2$, $VCl_3$, $VOCl_2$, $MnCl_2$, $MnCl_3$, $FeCl_2$, $FeCl_3$, $RuCl_3$, $COCl_2$, $RhCl_2$, $RhCl_3$, $NiCl_2$, $PdCl_2$, $PtCl_2$, $CuCl$, $CuCl_2$, and other chlorides, or fluorides, bromides or iodides each corresponding to these chlorides (e.g., $MnF_2$, $MnBr_2$, $MnF_3$, $FeF_2$, $FeF_3$, $FeBr_2$, $FeBr_3$, $FeI_2$, $CuBr$, $CuBr_2$), and other halides, $M^1MnCl_3$, $M^1{}_2MnCl_4$, $M^1{}_2MnCl_5$, $M^1{}_2MnCl_6$, wherein $M^1$ represents a monovalent metal, and other complex halides.

The ligand constituting the complex includes, for example, OH (hydroxo), methoxy, ethoxy, propoxy, butoxy and other alkoxy groups, acetyl, propionyl and other acyl groups, methoxycarbonyl (acetato), ethoxycarbonyl and other alkoxycarbonyl groups, acetylacetonato, cyclopentadienyl group, chlorine, bromine and other halogen atoms, CO, CN, oxygen atom, $H_2O$ (aquo), phosphine (e.g., triphenylphosphine and other triarylphosphine) and other phosphorus compounds, $NH_3$ (ammine), NO, $NO_2$ (nitro), $NO_3$ (nitrato), ethylenediamine, diethylenetriamine, pyridine, phenanthroline and other nitrogen-containing compounds. In the complexes or complex salts, the same or different ligands may be coordinated singly or in combination.

The ligand is practically, for example, OH, an alkoxy group, an acyl group, an alkoxycarbonyl group, acetylacetonato, a halogen atom, CO, CN, $H_2O$ (aquo), triphenylphosphine or other phosphorus compounds, or a nitrogen-containing compound inclusive of $NH_3$, $N_{O2}$ and $NO_3$.

The transition metal element and the ligand may optionally be employed in combination to form a complex. Such a complex includes, for instance, acetylacetonato complexes [e.g., acetylacetonato complex of Ce, Sm, Ti, Zr, V, Cr, Mo, Mn, Fe, Ru, Co, Ni, Cu or Zn, titanylacetylacetonato complex $TiO(AA)_2$, zirconylacetylacetonato complex $ZrO(AA)_2$, vanadylacetylacetonato complex $VO(AA)_2$], cyano complexes [e.g., hexacyanomanganate(I), hexacyanoferrate(II)], carbonyl complexes or cyclopentadienyl complexes [e.g., tricarbonylcyclopentadienylmanganese(I), biscyclopentadienylmanganese(II), biscyclopentadienyliron (II), $Fe(CO)_5$, $Fe_2(CO)_9$, $Fe_3(CO)_{12}$], nitrosyl compounds [e.g., $Fe(NO)_4$, $Fe(CO)_2(NO)_2$], thiocyanato complexes [e.g., thiocyanatocobalt, thiocyanatomanganese, thiocyanatoiron], or acetyl complexes [e.g. cobalt acetate, manganese acetate, iron acetate, copper acetate, zirconyl acetate $ZrO(OAc)_2$, titanyl acetate $TiO(OAc)_2$, vanadyl acetate $VO(OAc)_2$].

The polyacid (isopolyacid or heteropolyacid) is practically at least one member selected from Group 5 elements and Group 6 elements of the Periodic Table of Elements, such as V (vanadic acid), Mo (molybdic acid) or W (tungstic acid), typically speaking. There is no particular limit as to the central atom, and it may be any of, for instance, Cu, Be, B, Al, Si, Ge, Sn, Ti, Th, N, P, As, Sb, V, Nb, Ta, Cr, Mo, W, S, Se, Te, Mn, I, Fe, Co, Ni, Rh, Os, Ir, Pt, or Cu. As illustrative examples of the heteropolyacid, there may be mentioned cobaltmolybdate, cobalttungstate, molybdenumtungstate, manganesemolybdate, manganesetungstate, manganesemolybdenumtungstate, vanadomolybdophosphate, manganesevanadiummolybdate, and manganesevanadomolybdophosphate. These co-catalysts may be employed independently or in combination.

In the constitutive metal compound of these co-catalysts, the valency of the element is not particularly restricted, and it may be about from two to six valencies. Use of a divalent transition metal compound (e.g., a divalent cobalt compound) as the co-catalyst sometimes enhances oxidation activity. By way of illustration, a catalytic system comprising the imide compound in combination with a divalent transition metal compound (e.g., a divalent cobalt compound) instead of a trivalent transition metal compound induces an oxidized product in a short time with high selectivity and yield.

Incidentally, the use of a compound containing at least one element selected from Group 4A elements (e.g., Ti, Zr), Group 6A elements (e.g., Cr, Mo) and Group 7A elements (e.g., Mn) of the Periodic Table of Elements inhibits inactivation (deactivation) of the catalyst (in particular the imide compound) even in severe reaction conditions. Therefore, the process insures oxidation of the substrate with oxygen or air with commercial advantages.

Further, the use of a compound containing the Group 4A element (e.g., Ti, Zr), Group 5A element (e.g., V), Group 6A element (e.g., Cr, Mo), Group 7A element (e.g., Mn) or Group 8 element (e.g., Fe, Co) of the Periodic Table of Elements as the co-catalyst results in remarkable enhancement of the oxidizing activity and provides effective oxidation of the substrate. By way of an example, a catalytic system comprising, as the co-catalyst, a compound containing the Group 5A element (e.g., V), Group 7A element (e.g., Mn) or Group 8 element (e.g., Co) of the Periodic Table of Elements has high activities. A catalytic system comprising, as the co-catalyst, a compound containing the Group 7A element (e.g., Mn) or Group 8 element (e.g., Fe) of the Periodic Table of Elements has high activities for the substrate and provides a corresponding oxide (e.g., an alcohol or a ketone) with high selectivity.

A combination use of the imide compound of the above formula (1) with the co-catalyst containing the Group 1B element of the Periodic Table of Elements (e.g., Cu) as the oxidation catalytic system insures great improvement of the selectivity in the oxidation reaction, and inhibits deactivation of the imide compound. Therefore, this combination is advantageous for commercial production.

Furthermore, a use of the oxidation catalytic system comprising a combination of the imide compound of the above formula (1), and plural co-catalysts [e.g., a compound containing the Group 7A element of the Periodic Table of Elements (e.g., a manganese compound), and a compound containing the Group 8 element of the Periodic Table of Elements (e.g., an iron compound)] sometimes has further enhanced catalytic activities and provides effective and efficient production of an oxide with high conversion and selectivity. In the above complexed catalysis, a ratio of the compound containing the Group 8 element of the Periodic Table of Elements (the second co-catalyst) is not particularly limited, and is, for instance, about 0.1 to 25 moles (e.g., about 0.1 to 20 moles), preferably about 0.2 to 15 moles, and more preferably about 0.5 to 10 moles relative to one mole of the compound containing the Group 7A element of the Periodic Table of Elements (the first co-catalyst).

The oxidation catalyst may be whichever of a homogeneous system or a heterogeneous system. The oxidation catalyst or oxidation catalytic system may be a solid catalyst comprising a catalytic component supported on a support or carrier, as well. As the support, use can be practically made of activated carbon, zeolite, silica, silica-alumina, bentonite, or other porous supports. In the solid catalyst, a supporting amount of the catalytic component may be such that a relative ratio of the imide compound of the formula (1) to 100 parts by weight of the support is about 0.1 to 50 parts by weight, preferably about 0.5 to 30 parts by weight and more preferably about 1 to 20 parts by weight. A ratio of the co-catalyst supported on the support is about 0.1 to 30 parts by weight, preferably about 0.5 to 25 parts by weight, and more preferably about 1 to 20 parts by weight, relative to 100 parts by weight of the support.

A relative ratio of the co-catalyst to the imide compound of the formula (1) may be selected from a wide range, an increasement of the amount of co-catalyst to the imide compound may deteriorate the activities of the imide compound considerably, thus high activities can not be sometimes maintained for a long time. Therefore, for the purpose of maintaining high activities of the oxidation catalyst, the oxidation catalyst preferably comprises the imide compound and the co-catalyst of not less than an effective amount to not more than about 10 mole e (e.g., about 0.01 to 10 mole %, preferably about 0.05 to 8 mole %, and more preferably about 0.1 to 7 mole %) relative to the imide compound, advantageously. The oxidation catalyst, generally, comprises the imide compound and about 0.1 to 8 mole % (specifically, about 1 to 5 mole %) of the co-catalyst relative to the imide compound.

The proportion of the imide compound of the formula (1) in the oxidation reaction (i.e., in the production of a ketone, an alcohol, an aldehyde or an alcohol) is selected from a broad range, and may for example be about 0.0001 to 1 mole (0.01 to 100 mole %), preferably about 0.001 to 0.5 mole (0.1 to 50 mole %), more preferably about 0.01 to 0.30 mole and practically about 0.01 to 0.25 mole, relative to 1 mole of the substrate, typically speaking.

Depending on the amount of the imide compound, the proportion of the co-catalyst (a co-oxidizing agent) used in such a reaction can be liberally selected from a range not interfering with the activity and selectivity, and is, for example, about 0.0001 mole (0.01 mole %) to 0.5 mole (50 mole %), preferably about 0.0001 to 0.3 mole, and more preferably about 0.001 to 0.2 mole relative to one mole of the substrate. The co-catalyst is practically used in a ratio of 0.0005 to 0.1 mole (e.g., about 0.005 to 0.1 mole) per one mole of the substrate.

[Substrate]

The use of the oxidation catalyst comprising the imide compound and the co-catalyst provides an alcohol or a ketone from a non-cyclic branched aliphatic hydrocarbon, efficiently.

Any compounds which is a non-cyclic branched aliphatic hydrocarbon (specifically, a saturated hydrocarbon) having a secondary carbon atom, in particular, a tertiary carbon atom (a methine carbon atom or a methylidine group) can be used as a substrate. A commercially useful hydrocarbon includes, for example, a branched aliphatic hydrocarbon having about 4 to 30 (preferably about 4 to 20, and more preferably about 4 to 16) carbon atoms.

The substrate includes a branched aliphatic hydrocarbon having about 4 to 12 carbon atoms (containing a branched chain having about 1 to 4 carbon atoms), such as isobutane, isopentane, isohexane, isoheptane, isooctane, isodekane, isododekane, 2,3-dimethylbutane, 2-methylpentane, 3-methylpentane, 2,3-dimethylpentane, 2,4-dimethylpentane, 2,3,4-trimethylpentane, 3-ethylpentane, 2-methylhexane, 3-methylhexane, 2,3-dimethylhexane, 2,4-dimethylhexane, 3,4-dimethylhexane, 2,5-dimethylhexane, 2,3,5-trimethylhexane, 2-propylhexane, 3-butylhexane, 2-methylheptane, 3-methylheptane, 4-methylheptane, 2-ethylheptane, 3-ethylheptane, 2,6-dimethylheptane, 2-methyloctane, 3-methyloctane, 2,7-dimethyloctane and 2-methylnonane. Preferred aliphatic hydrocarbon comprises a branched aliphatic hydrocarbon having about 4 to 10 carbon atoms, preferably about 4 to 8 carbon atoms, and specifically about 4 to 6 carbon atoms including the carbon number of a branched chain.

These substrates may have any of various substituents. Examples of such substituents include halogen atoms (iodine, bromine, chlorine and fluorine atoms), an oxo group, a hydroxyl group, alkoxy groups (e.g., methoxy, ethoxy, propoxy, isopropoxy, butoxy, isobutoxy, t-butoxy, hexyloxy and other alkoxy groups having about 1 to 6 carbon atoms, in particular lower alkoxy groups having about 1 to 4 carbon atoms), hydroxyalkyl groups (e.g., hydroxymethyl, 2-hydroxyethyl and other hydroxy-$C_{1-4}$ alkyl groups), a carboxyl group, alkoxycarbonyl groups (e.g., methoxycarbonyl, ethoxycarbonyl, propoxycarbonyl, isopropoxycarbonyl, butoxycarbonyl, isobutoxycarbonyl, t-butoxycarbonyl, hexyloxycarbonyl and other alkoxycarbonyl groups having about 1 to 6 carbon atoms in the alkoxy moiety, in particular lower alkoxycarbonyl groups having about 1 to 4 carbon atoms in the alkoxy moiety), acyl groups (e.g., formyl, acetyl, propionyl, butyryl, isobutyryl, valeryl, isovaleryl, pivaloyl, and other acyl groups having about 1 to 6 carbon atoms), an amino group, a substituted amino group, a cyano group, a nitro group and the like.

Further, the branched hydrocarbon may be substituted with a cyclic hydrocarbon group, such as a terpene (e.g., menthane, menthene, thujane and thujen), as far as the hydrocarbon has a secondary carbon atom, specifically, a tertiary carbon atom at the non-cyclic site.

[Oxidation reaction]

The oxygen used in oxidation of the substrate may be active oxygen, but molecular oxygen is practically employed for economical advantages. Such molecular oxygen is not specifically limited, and use may be made of whichever of pure oxygen, or oxygen diluted with an inert gas such as nitrogen, helium, argon or carbon dioxide gas. Air is preferably employed from the viewpoints of handling property and safety, and economical property.

An amount of oxygen can be selected from a range according to the species of the substrate, and usually is, 0.5 mole or more (e.g., 1 mole or more), preferably about 1 to 100 moles, and more preferably about 2 to 50 moles relative to 1 mole of the substrate. The oxygen is practically used in an excess mole relative to the substrate. In specific, the reaction is advantageously carried out in an atmosphere containing molecular oxygen such as air or oxygen gas.

Oxidation process of the invention is generally conducted in an inert organic solvent. As the organic solvents, there may be mentioned, for example, formic acid, acetic acid, propionic acid and other organic carboxylic acids or hydroxycarboxylic acids, acetonitrile, propionitrile, benzonitrile and other nitriles, formamide, acetamide, dimethylformamide (DMF), dimethylacetamide and other amides, t-butanol, t-amyl alcohol and other alcohols, hexane, octane and other aliphatic hydrocarbons, benzene and other aromatic hydrocarbons, chloroform, dichloromethane, dichloroethane, carbon tetrachloride, chlorobenzene and other halogenated hydrocarbons, nitrobenzene, nitromethane, nitroethane and other nitro compounds, ethyl acetate, butyl acetate and other esters, dimethyl ether, diethyl ether, diisopropyl ether, dioxane and other ethers, and mixtures of these solvents. Incidentally, the substrate may be employed as the reaction solvent, if used in an excess amount. Use may practically be made of, as the solvent, acetic acid or other organic acids, acetonitrile, benzonitrile or other nitriles.

In the present invention, the oxidation reaction in the presence of a non-protonic compound provides an alcohol from the branched hydrocarbon advantageously, and the oxidation reaction in the presence of a protonic acid improves the formation efficiency of a ketone from the branched hydrocarbon. The non-protonic compound or the protonic acid may be any of the solvent listed above. According to the preferred process of the present invention, a branched alcohol (especially, a tertiary alcohol) corresponding to a branched hydrocarbon (especially, a hydrocarbon having a tertiary carbon atom) is formed in the presence of non-protic solvent (especially, a non-protic polar solvent).

The non-protonic compound (non-protic solvent) includes a nitrile (e.g., acetonitrile, propionitrile, benzonitrile), an amide [e.g., formamide, acetamide, demethylformamide (DMF), dimethylacetamide], halogenated hydrocarbon (e.g., chloroform, dichloromethane, dichloroethane, tetrachloroethane, chlorobenzene), a nitro compound (e.g., nitrobenzene, nitromethane, nitroethane), an ether (e.g., dimethylether, diethylether, diisopropylether, dioxane), a sulfoxide (e.g., dimethylsulfoxide), N-methylpyrrolidone, hexamethylphosphoryl amide (HMPA), and a mixture thereof.

As the proton acid, there may be exemplified organic acids (e.g., formic acid, acetic acid, propionic acid and other organic carboxylic acids, oxalic acid, citric acid, tartaric acid and other hydroxycarboxylic acids, methanesulfonic acid, ethanesulfonic acid and other alkylsulfonic acids, benzenesulfonic acid, p-toluenesulfonic acid and other arylsulfonic acids), and inorganic acids (e.g., hydrochloric acid, sulfuric acid, nitric acid, phosphoric acid).

The process of the invention is characterized in that the oxidation reaction smoothly proceeds even in comparatively mild or moderate conditions. A reaction temperature can be voluntarily selected according to the species of the substrate and the catalyst. The temperature is, for instance, about 30 to 200° C., preferably about 50 to 150° C., more preferably about 60 to 120° C., and practically about 70 to 110° C.

The reaction may be carried out at ambient pressure (atmospheric pressure) or under a pressure (under a load). When the reaction is conducted under a pressure, the pressure is, usually, about 1 to 100 atm (e.g., about 1.5 to 80 atm), preferably about 2 to 70 atm, and more preferably about 5 to 50 atm under an oxygen or air atmosphere. A reaction time can be liberally chosen within a range of about 30 minutes to 48 hours, preferably about 1 to 36 hours, and more preferably about 2 to 24 hours, according to the reaction temperature and pressure.

The reaction may be effected in a conventional manner such as in a batch system, semi-batch system or continuous system, in the presence of molecular oxygen or under flow of molecular oxygen. After completion of the reaction, a reaction product can easily be isolated and purified according to a conventional technology, such as filtration, condensation, distillation, extraction, crystallization, recrystallization, column chromatography, or other isolation means, or a combination of these technologies.

The present invention can effectively oxidize a non-cyclic branched aliphatic hydrocarbon with oxygen to give a corresponding alcohol or ketone since the specific oxidation catalyst is used. Incidentally, the present invention can efficiently oxidize the non-cyclic branched aliphatic hydrocarbon with inhibiting the catalytic activities and can provide a branched alcohol or ketone with high transformation rate or conversion and selectivity. Particularly, the present invention is useful to produce a tertiary alcohol by the oxidation with oxygen with high transformation rate or conversion and selectivity.

EXAMPLES

The following examples are intended to describe the present invention in more detail, but should by no means be construed to limit the scope of the invention.

Example 1

To benzonitrile was added 5 mmol of isobutane, 0.5 mmol of N-hydroxyphthalimide (NHPI) and 0.0125 mmol of cobalt acetate Co(OAc)$_2$, and the resultant mixture was stirred under an air atmosphere at a pressure of 10 atm and at a temperature of 100° C. for 8 hours. The products in the reaction mixture were analyzed by gas chromatography, and, as a result, t-butanol (yield 81%) and acetone (yield 14%) were formed.

Example 2

The reaction was conducted in the same manner as Example 1 except that the stirring was effected for 4 hours, and, as a result, t-butanol (yield 67%) and acetone (yield 11%) were formed.

Example 3

The reaction was conducted in the same manner as Example 1 except using acetic acid instead of benzonitrile, and, as a result, t-butanol (yield 21%) and acetone (yield 22%) were formed.

Example 4

The reaction was conducted in the same manner as Example 1 except that the stirring was effected at a pressure of 5 atm to give t-butanol (yield 63%) and acetone (yield 11%).

Example 5

The reaction was carried out in the same manner as Example 1 except that the stirring was effected at a temperature of 800° C., and, as a result, t-butanol (yield 63%) and acetone (yield 8%) were formed.

Example 6

The reaction was carried out in the same manner as Example 1 except using 0.25 mmol of NHPI instead of 0.5 mmol of NHPI, and, as a result, t-butanol (yield 66%) and acetone (yield 16%) were formed.

Example 7

The reaction was effected in the same manner as Example 1 except using 0.0125 mmol of vanadyl(II) acetylacetonato VO(AA)$_2$ instead of 0.0125 mmol of Co(OAc)$_2$, and, as a result, t-butanol (yield 25%) and acetone (yield 10%) were formed.

Example 8

The reaction was effected in the same manner as Example 1 except using 0.0125 mmol of acetylacetonatocobalt(II) Co(AA)$_2$ instead of 0.0125 mmol of Co(OAc)$_2$, and, as a result, t-butanol (yield 84%) and acetone (yield 13%) were formed.

Example 9

The reaction was effected in the same manner as Example 1 except using 0.0125 mmol of acetylacetonatocobalt(III) Co(AA)$_3$ instead of 0.0125 mmol of Co(OAc)$_2$, and, as a result, t-butanol (yield 58%) and acetone (yield 10%) were formed.

Example 10

To benzonitrile was added 5 mmol of isobutane, 0.5 mmol of NHPI and 0.0125 mmol of cobalt acetate Co(OAc)$_2$, and the resultant mixture was stirred under an oxygen atmosphere at a pressure of 1 atm and at a temperature of 100° C. for 24 hours. As a result, t-butanol (yield 18%) and acetone (yield 4%) were formed.

Example 11

To benzonitrile was added 5 mmol of isobutane, 0.05 mmol of NHPI and 0.0125 mmol of cobalt acetate Co(OAc)$_2$, and the resultant mixture was stirred under an air atmosphere at a pressure of 10 atm and at a temperature of 100° C. for 24 hours. As a result, t-butanol (yield 22%) and acetone (yield 10%) were formed.

Example 12

To benzonitrile was added 5 mmol of isobutane, 0.05 mmol of NHPI and 0.0125 mmol of cobalt acetate Co(OAc)$_2$, and the resultant mixture was stirred under an air atmosphere at a pressure of 10 atm and at a temperature of 50° C. for 55 hours. As a result, t-butanol (yield 32%) and acetone (yield 5%) were formed.

Example 13

The reaction was effected in the same manner as Example 1 except using 0.0125 mmol of titanylacetylacetonato TiO(AA)$_2$ instead of 0.0125 mmol of Co(OAc)$_2$, and, as a result, t-butanol (yield 6%) and acetone (yield 2%) were formed.

Example 14

The reaction was effected in the same manner as Example 1 except using 0.0125 mmol of acetylacetonatovanadium V(AA)$_3$ instead of 0.0125 mmol of Co(OAc)$_2$, and, as a result, t-butanol (yield 18%) and acetone (yield 9%) were formed.

Example 15

The reaction was effected in the same manner as Example 1 except using 0.0125 mmol of acetylacetonatochromium Cr(AA)$_3$ instead of 0.0125 mmol of Co(OAc)$_2$, and, as a result, t-butanol (yield 52%) and acetone (yield 9%) were formed.

Example 16

The reaction was effected in the same manner as Example 1 except using 0.0125 mmol of acetylacetonatomanganese (II) Mn(AA)$_2$ instead of 0.0125 mmol of Co(OAc)$_2$, and, as a result, t-butanol (yield 28%) and acetone (yield 8%) were formed.

Example 17

The reaction was effected in the same manner as Example 1 except using 0.0125 mmol of acetylacetonatomanganese (III) Mn(AA)$_3$ instead of 0.0125 mmol of Co(OAc)$_2$, and, as a result, t-butanol (yield 48%) and acetone (yield 12%) were formed.

Example 18

The reaction was effected in the same manner as Example 1 except using 0.0125 mmol of acetylacetonatoiron Fe(AA)$_3$ instead of 0.0125 mmol of Co(OAc)$_2$, and, as a result, t-butanol (yield 52%) and acetone (yield 9%) were formed.

Example 19

The reaction was effected in the same manner as Example 1 except using 0.0125 mmol of acetylacetonatonickel Ni(AA)$_2$ instead of 0.0125 mmol of Co(OAc)$_2$, and, as a result, t-butanol (yield 25%) and acetone (yield 6%) were formed.

Example 20

The reaction was effected in the same manner as Example 1 except using 0.0125 mmol of acetylacetonatocopper Cu(AA)$_2$ instead of 0.0125 mmol of Co(OAc)$_2$, and, as a result, t-butanol (yield 47%) and acetone (yield 11%) were formed.

What is claimed is:

1. An oxidation process comprises contacting a non-cyclic branched aliphatic hydrocarbon with oxygen in the presence of an oxidation catalyst, wherein said oxidation catalyst comprises;

an imide compound shown by the following formula

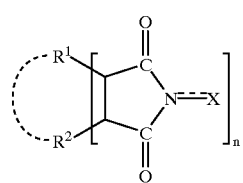

(1)

wherein R$^1$ and R$^2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or R$^1$ and R$^2$ may together form a double bond or an aromatic or non-aromatic ring; X represents an oxygen atom or a hydroxyl group; and n denotes an integer of 1 to 3, or said imide compound and a co-catalyst.

2. An oxidation process according to claim 1, wherein the branched aliphatic hydrocarbon is a saturated aliphatic hydrocarbon having a tertiary carbon atom.

3. An oxidation process according to claim 1, wherein the ratio of the co-catalyst is in a range of not less than an effective amount to not more than 10 mole % relative to the imide compound.

4. An oxidation process according to claim 1, wherein the co-catalyst comprises an element selected from the group consisting of Group 2A elements of the Periodic Table of Elements, transition metal and Group 3B elements of the Periodic Table of Elements.

5. An oxidation process according to claim 1, wherein the co-catalyst is a transition metal compound which comprises an element selected from the group consisting of Group 3A elements, Group 4A elements, Group 5A elements, Group 6A elements, Group 7A elements, Group 8A elements and Group 1B elements of the Periodic Table of Elements.

6. An oxidation process according to claim 1, wherein said co-catalyst contains an element selected from the group consisting of lanthanoids, Ti, Zr, V, Cr, Mo, W, Mn, Fe, Ru, Co, Rh, Ni and Cu.

7. A process for producing an oxide which comprises the step of contacting a non-cyclic branched aliphatic hydrocarbon with oxygen in the presence of an oxidation catalyst claimed in claim 1 to give an alcohol or a ketone each corresponding to the hydrocarbon.

8. A process for producing an oxide according to claim 7, wherein a non-cyclic branched aliphatic hydrocarbon is contacted with oxygen in the presence of a non-protic solvent to give an alcohol corresponding to the branched aliphatic hydrocarbon.

9. A process for producing an oxide according to claim 7, wherein the proportion of the co-catalyst is from not less than an effective amount to not more than 10 mole % relative to the imide compound, and the reaction temperature is 60 to 120° C.

10. A process for producing an oxide according to claim 7, wherein a non-cyclic branched saturated C$_{4-6}$ aliphatic hydrocarbon having a tertiary carbon atom is contacted with oxygen with use of 0.05 to 8 mole % of the co-catalyst relative to the imide compound to produce an alcohol and a ketone corresponding to the aliphatic hydrocarbon.

11. A process for producing an oxide which comprises the step of contacting a non-cyclic branched saturated aliphatic hydrocarbon having a tertiary carbon atom with oxygen in the presence of an oxidation catalyst comprising an imide compound and a cocatalyst to produce an alcohol and a ketone corresponding to the aliphatic hydrocarbon, wherein the imide compound is of the following formula:

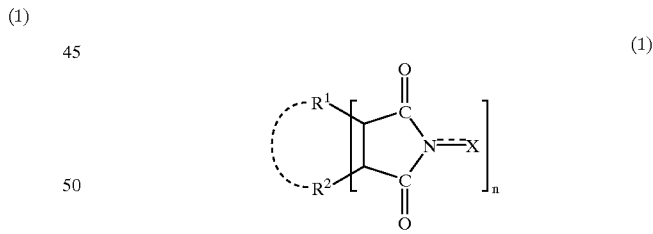

(1)

wherein R$^1$ and R$^2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or R$^1$ and R$^2$ may together form a double bond or an aromatic or non-aromatic ring; X represents an oxygen atom or a hydroxyl group; and n denotes an integer of 1 to 3, and wherein the amount of cocatalyst relative to the imide compound is 0.01 to 1 mole %.

12. The oxidation process according to claim 1, wherein the ratio of the co-catalyst is in a range of 0.01 to 10 mole % relative to the imide compound.

13. The process for producing an oxide according to claim 7, wherein the proportion of the co-catalyst is 0.01 to 10 mole % relative to the imide compound, and the reaction temperature is 60 to 120° C.

14. An oxidation process comprising the step of contacting a non-cyclic branched saturated aliphatic hydrocarbon having a tertiary carbon atom with oxygen in the presence of an oxidation catalyst,
wherein said oxidation catalyst comprises an imide compound without a co-catalyst wherein the imide compound is shown by the following formula:

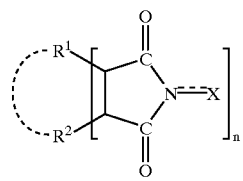

(1)

wherein $R^1$ and $R^2$ independently represent a hydrogen atom, a halogen atom, an alkyl group, an aryl group, a cycloalkyl group, a hydroxyl group, an alkoxy group, a carboxyl group, an alkoxycarbonyl group, or an acyl group, or $R^1$ and $R^2$ may together form a double bond or an aromatic or non-aromatic ring; X represents an oxygen atom or a hydroxyl group; and n denotes an integer of 1 to 3.

15. An oxidation process according to claim 1, wherein the non-cyclic branched aliphatic hydrocarbon has 4 to 30 carbon atoms.

16. A process for producing an oxide according to claim 7, wherein the non-cyclic branched aliphatic hydrocarbon has 4 to 30 carbon atoms.

17. An oxidation process according to claim 1, wherein the non-cyclic branched aliphatic hydrocarbon has 4 to 6 carbon atoms.

18. A process for producing an oxide according to claim 7, wherein the non-cyclic branched aliphatic hydrocarbon has 4 to 6 carbon atoms.

19. An oxidation process according to claim 1, wherein the non-cyclic branched aliphatic hydrocarbon is isobutane.

20. A process for producing an oxide according to claim 7, wherein the non-cyclic branched aliphatic hydrocarbon is isobutane.

* * * * *